United States Patent [19]

Mai et al.

[11] Patent Number: 4,990,668

[45] Date of Patent: Feb. 5, 1991

[54] OPTICALLY ACTIVE ARYLOXYPROPANOLAMINES AND ARYLETHANOLAMINES

[75] Inventors: Khuong H. X. Mai, Waukegan; Ghanshyam Patil, Vernon Hills; William L. Matier, Libertyville, all of Ill.

[73] Assignee: E. I. Du Pont de Nemours and Company, Wilmington, Del.

[21] Appl. No.: 804,407

[22] Filed: Dec. 4, 1985

[51] Int. Cl.$^5$ .................... C07C 215/08; C07C 217/54
[52] U.S. Cl. ..................... 564/349; 544/134; 544/169; 544/224; 544/312; 546/159; 548/135; 548/186; 548/247; 548/305; 548/444; 548/503; 548/509; 548/515; 549/23; 549/289; 549/304; 549/387; 549/466; 549/468; 549/487; 549/491; 558/401; 558/422; 560/29; 560/38; 560/42; 564/51; 564/79; 564/86; 564/165; 564/220; 564/363
[58] Field of Search ............... 544/134, 169, 224, 312; 546/158; 548/135, 186, 247, 305, 444, 503, 504, 515; 549/23, 289, 304, 387, 466, 468, 487, 491; 558/401, 422; 560/29, 35, 42; 564/51, 86, 165, 220, 79, 363, 349

[56] References Cited

U.S. PATENT DOCUMENTS 3,850,946 11/1974 Edwards .......................... 564/374 X
4,202,978 5/1980 Fohrenholtz et al. ........... 564/349 X
4,582,905 4/1986 Sakai ................................ 564/349 X

FOREIGN PATENT DOCUMENTS 56-123854 9/1981 Japan .................................. 564/349

OTHER PUBLICATIONS

Iriuchijima et al., "Agric. Biol. Chem.", vol. 46, No. 5, pp. 1153-1157 (1982).

*Primary Examiner*—Richard L. Raymond
*Attorney, Agent, or Firm*—Gildo E. Fato

[57] ABSTRACT

Described is a process for preparing a racemic or chiral aryloxypropanolamine (1) or arylethanolamine (2) of the formula

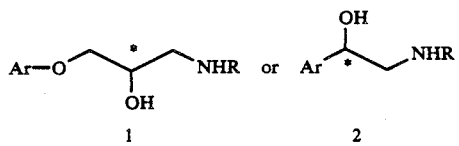

wherein Ar is aryl, substituted aryl, heteroaryl, or aralkyl and R is alkyl, substituted alkyl, aralkyl, or WB wherein W is a straight or branched chain alkylene of from 1 to about 6 carbon atoms and wherein B is $-NR_2COR_3$, $-NR_2CONR_3R_4$, $-NR_2SO_2R_3$, $-NR_2SO_2NR_3R_4$, or $-NR_2COOR_5$, where $R_2$, $R_3$, $R_4$, and $R_5$ may be the same or different and may be hydrogen, alkyl, alkoxyalkyl, alkoxyaryl, cycloalkyl, alkenyl, alkynyl, aryl, heteroaryl, or aralkyl, except that $R_3$ and $R_5$ are not hydrogen when B is $-NR_2SO_2R_3$ or $-NR_3COOR_5$, or $R_3$ and $R_4$ may together with N form a 5- to 7-membered heterocyclic group.

The process can be used to prepare beta-blocking agents, useful in the treatment of cardiac conditions.

7 Claims, No Drawings

OPTICALLY ACTIVE ARYLOXYPROPANOLAMINES AND ARYLETHANOLAMINES

BACKGROUND OF THE INVENTION

Aryloxypropanolamines (1) and arylethanolamines (2) are widely used therapeutic agents, particularly those compounds possessing potent beta-adrenergic receptor blocking activity. These beta-adrenergic blocking agents are widely used for a number of cardiovascular therapeutic indications, such as hypertension, angina pectoris, cardiac arrhythmias, myocardial infarction and more recently in the treatment of glaucoma. In addition, certain aryloxypropanolamines possess potent beta-adrenergic stimulating properties and such compounds are used as cardiac stimulants.

Among beta-blocker oxypropanolamines, the R isomers are less active or essentially devoid of beta-blocking activity as compared to their counterpart S isomers. Similarly, the R-isomer beta-agonists are more potent agents than their S-isomer counterparts.

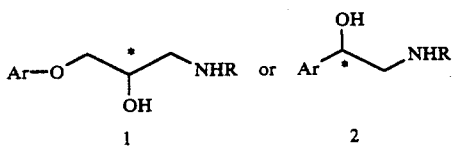

1        2

Conventional methods for preparing such compounds utilize the hydrolysis of the ketal 3 to give the diol 4 followed by the HBr/AcOH treatment to provide the bromoacetoxy 5. Subsequently, the bromoacetoxy 5 is transformed into an epoxide which is then treated with the corresponding amine to provide the desired beta-blocker in separate stages. Such a procedure is described by S. Iriuchijima and N. Kojima, Agric. Biol. Chem. 46 (5), 1153 (1982). In such a procedure, to prepare the optically active aryloxypropanolamines, four steps are required, starting from the ketal 3. An efficient and an economical process for preparing the separate isomers is therefore highly desirable.

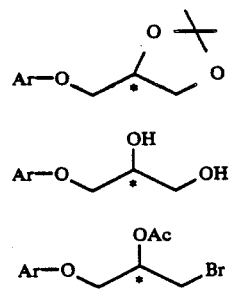

SUMMARY OF THE INVENTION

In accordance with the present invention, disclosed is a process for preparing a racemic or chiral aryloxypropanolamine (1) or arylethanolamine (2) of the formula

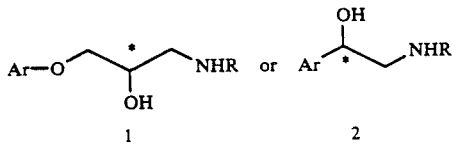

1        2 wherein Ar is aryl, substituted aryl, heteroaryl, or aralkyl and R is alkyl, substituted alkyl, aralkyl, or EG wherein E is a straight or branched chain alkylene of from 1 to about 6 carbon atoms and wherein G is $-NR_2COR_3$, $-NR_2CONR_3R_4$, $-NR_2SO_2R_3$, $-NR_2SO_2NR_3R_4$, or $-NR_2COOR_5$, where $R_2$, $R_3$, $R_4$, and $R_5$ may be the same or different and may be hydrogen, alkyl, alkoxyalkyl, alkoxyaryl, cycloalkyl, alkenyl, alkynyl, aryl, heteroaryl, or aralkyl, except that $R_3$ and $R_5$ are not hydrogen when G is $-NR_2SO_2R_3$ or $-NR_2COOR_5$, or $R_3$ and $R_4$ may together with N form a 5- to 7-membered heterocyclic group.

As an example, a specific embodiment of the method involves the utilization of an HBr/acetic acid (AcOH) mixture to directly convert the ketal 3 to the bromoacetoxy 5 without going through the intermediate diol 4. The bromoacetoxy 5 is then allowed to react with a selected amine in an alcoholic medium to provide the desired aryloxypropanolamine. An alternative procedure for the latter reaction is to convert the bromoacetoxy 5 to an epoxide followed by amination. The method offers the convenience of fewer reaction steps. More generally, a mixture of a strong acid, HX, where X is chloro, bromo or iodo, in an amount of from 0.1 to 50% in an organic acid, Y—COOH where Y is hydrogen, loweralkyl or cycloalkyl, is used to convert the ketal 3.

DETAILED DESCRIPTION OF THE INVENTION

In accordance with the present invention, disclosed is a process for preparing optically active aryloxypropanolamines (1) or arylethanolamines (2) of the formula

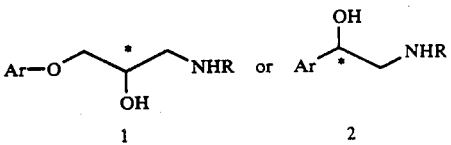

1        2 wherein Ar is aryl, substituted aryl, heteroaryl or aralkyl and R is alkyl, substituted alkyl, aralkyl, or EG wherein E is a straight or branched chain alkylene of from 1 to about 6 carbon atoms and wherein B represents $-NR_2COR_3$, $-NR_2CONR_3R_4$, $-NR_2SO_2R_3$, $-NR_2SO_2NR_3R_4$, or $-NR_2COOR_5$ wherein $R_2$, $R_3$, $R_4$ and $R_5$ may be the same or different and may be hydrogen, alkyl of from 1 to about 10 carbon atoms and preferably from 1 to about 6 carbon atoms, alkoxyalkyl wherein the alkyl groups may be the same or different and contain from 1 to about 10 carbon atoms and preferably from 1 to about 6 carbon atoms; cycloalkyl of from 3 to about 8 carbon atoms, alkenyl of from 3 to about 10 carbon atoms, alkoxyaryl wherein the alkyl group contains from 1 to about 6 carbon atoms, alkynyl of from 3 to about 10 carbon atoms, aryl which includes substituted or unsubstituted monocyclic or polycyclic aromatic or heterocyclic ring systems of from 6 to about 10 carbon atoms such as phenyl, thienyl, imidazole, oxazole, indole, and the like, or aralkyl wherein the alkyl portion contains from 1 to about 6 carbon atoms and the aryl portion represents substituted or unsubstituted monocyclic or polycyclic aromatic or heterocyclic ring systems of from 5 to about 10 carbon atoms such as benzyl, phenethyl, 3,4-dimethoxyphenethyl, 1,1-dimethyl-2-(3-indolyl)ethyl and the like; except that $R_3$ and $R_5$ are not hydrogen when G is $-NR_2SO_2R_3$ or $-NR_2COOR_5$, or $R_3$ and $R_4$ may together with N form a 5- to 7-membered heterocyclic group such as pyrrolidine, piperidine, piperazine, morpholine, or thiomorpholine.

As used herein, the term "aryl" represents a phenyl or naphthyl group which may be unsubstituted or substituted with alkyl of from 1 to about 6 carbon atoms, alkenyl of from 2 to about 6 carbon atoms, alkynyl of from 2 to about 10 carbon atoms, alkoxy wherein the alkyl group contains from 1 to about 6 carbon atoms, halo, acetamido, amino, amido, nitro, alkylamino of from 1 to about 6 carbon atoms, hydroxy, hydroxyalkyl of from 1 to about 6 carbon atoms, cyano or arylalkoxy wherein the alkyl group contains from 1 to about 6 carbon atoms and the aryl group is substituted or unsubstituted phenyl.

The term "heteroaryl" as used herein represents pyridine, pyrazine, pyrrole, pyrazole, piperazine, thiophene, benzothiophene, furan, benzofuran, imidazole, oxazole, indole, carbazole, thiazole, thiadiazole, benzothiadiazole, triazole, tetrazole, azepine, 1,2-diazepine, or 1,4-thiazepine. Preferably, the heteroaryl is selected from the group consisting of pyridine, pyrazine, thiophene, benzothiophene, benzofuran, indole, carbazole, thiadiazole or benzothiadiazole, with the most preferred being pyrazine, indole, 1,2,5-thiadiazole, or benzofuran.

The term "heterocyclic" as used herein represents pyrrolidine, piperidine, morpholine, or thiomorpholine.

In the term "aralkyl" as used herein, the alkyl group contains from about 1 to about 6 carbon atoms and the aryl group represents substituted or unsubstituted monocyclic or polycyclic aromatic or heterocyclic ring systems of from 5 to about 10 carbon atoms, such as benzyl, phenethyl, 3,4-dimethoxyphenethyl, 1,1-dimethyl-2-(3-indolyl)-ethyl and the like. Aromatic (Ar) substituents may include lower alkyl of from 1 to about 10 carbon atoms, alkenyl of from 2 to about 10 carbon atoms, alkynyl of from 2 to about 10 carbon atoms, alkoxy wherein the alkyl group contains from 1 to about 10 carbon atoms, halo, acetamido, amino, nitro, alkylamino of from 1 to about 10 carbon atoms, hydroxy, hydroxyalkyl of from 1 to about 10 carbon atoms, cyano, arylalkoxy wherein the alkyl group contains from 1 to about 6 carbon atoms and the aryl group represents substituted or unsubstituted phenyl and groups of the formula

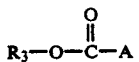

wherein $R_3$ is lower alkyl, aryl or aralkyl and A is a direct bond, alkylene of from 1 to about 10 carbon atoms or alkenylene of from 2 to about 10 carbon atoms.

The term "cycloalkyl" as used herein refers to cyclic saturated aliphatic radicals containing 3 to 6 carbon atoms in the ring, such as cyclopropyol, cyclobutyl, cyclopentyl or cyclohexyl.

As an example, the method involves the utilization of an HBr/AcOH mixture to directly convert the aryloxypropanolamine. The method can be used in the synthetic of beta-agonists or beta-blockers.

The following reaction schemes summarize the process of the present invention.

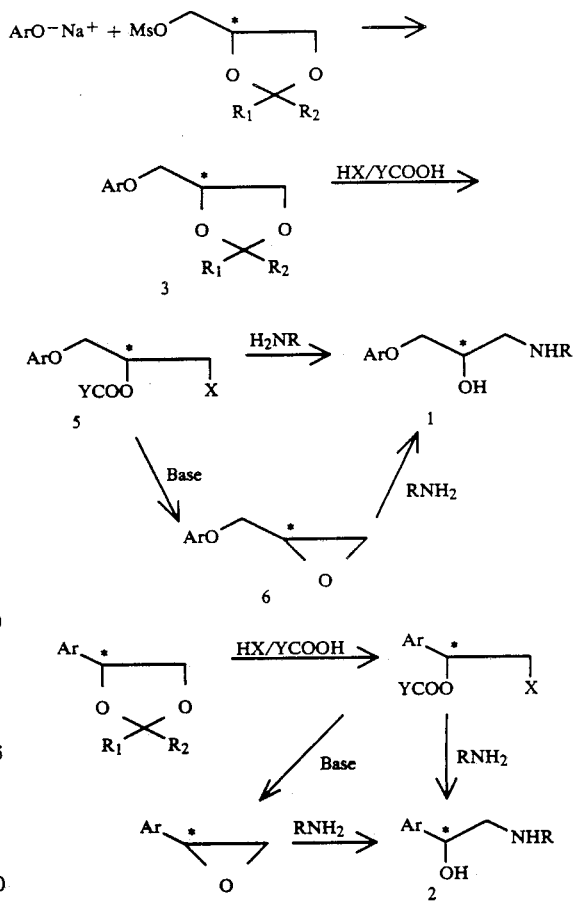

Referring to the scheme, the (R)-(−) or S-(+)-2,2-dimethyl-4-aryloxymethyl-1,3-dioxolane (3) can be made by known methods. For example, the S-enantiomer can be prepared readily by reacting an appropriate phenoxide with S-(+)-2,2-dimethyl-4-(hydroxymethyl)-1,3- dioxolane methanesulfonate or p-toluene-sulfonate.

The aryloxypropanolamine (1) can be made by reacting the above dioxolane (or ketal) with NBr/Acetic acid, followed by amination with a selected amine.

If desired, the bromoacetoxy 5 is allowed to react with a suitable base to give the epoxide 6, which is then reacted with a selected amine to prepare the desired aryloxypropanolamine.

A suitable base for reaction with the bromoacetoxy would be a metal alkoxide, metal hydroxide, metal hydride, metal carbonate or metal bicarbonate wherein the metal is sodium, potassium or calcium, or an ammonium hydroxide or a suitable organic base. Preferred organic bases are pyridine, dimethylaminopyridine, dimethylaniline, quinoline, 1,8-Diazabicyclo[5.4.0]undec-7-ene (DBU), 1,5-Diazabicyclo[4,3.0]non-5-ene (DBN) or tertiary alkylamines. Preferred bases are sodium or potassium methoxide, ethoxide or t-butoxide or a tertiary alkyl amine.

The arylethanolamines can be prepared as follows. The aryl ketal of 1,2-ethanediol can be converted to the corresponding bromoacetate by reacting it with HBr/AcOH. The resulting bromohydrin then can be cyclized to an epoxide by treating it with one equivalent of sodium methoxide. The arylethanolamine can be obtained by treating the epoxide with one equivalent of amine.

The following beta-adrenergic blocking agents, beta-agonists and partial agonists are representative of the compounds that can be made using the described process:

| Ar | R | Compound |
|---|---|---|
| (Ar—O—CH₂—CH(OH)—CH₂—NH—R) | | |
| 4-methyl-3-acetyl-5-(butanamido)phenyl | + (isopropyl) | Acebutolol |
| 1-naphthyl | —CH₂CH₂—N(phenyl)—C(=O)—NH— (tert) | Adimolol |
| 2-methyl-(phthalide)phenyl | + (isopropyl) | Afurolol |
| 2-(allyl)phenyl (CH₂CH=CH₂) | isopropyl | Alprenolol |
| 2-(furan-2-carboxamido)phenyl | + (isopropyl) | Ancarolol |
| 4-(CH₂CONH₂)phenyl | isopropyl | Atenolol |
| 7-methyl-benzofuran-2-yl-COCH₃ | isopropyl | Befunolol |
| 4-(CH₂CH₂O—CH₂-cyclopropyl)phenyl | isopropyl | Betaxolol |

-continued
| | | |
|---|---|---|
| 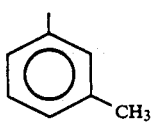 | 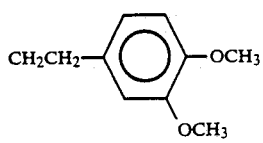 | Bevantolol |
| 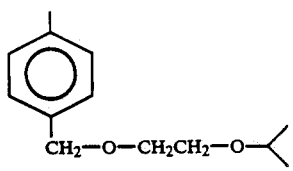 |  | Bisprolol |
| 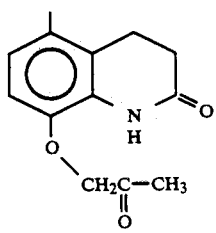 | 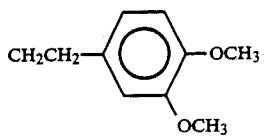 | Bometolol |
| 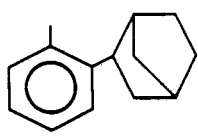 |  | Bornaprolol |
| 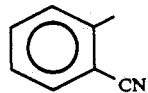 | 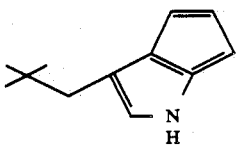 | Bucindolol |
| 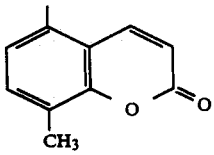 |  | Bucumolol |
| 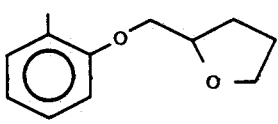 |  | Bufetolol |
| 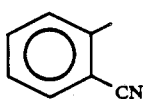 |  | Bunitrolol |
| 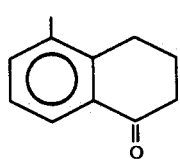 |  | Bunalol |

-continued

| Structure | | Name |
|---|---|---|
| (3-chloro-4-methylphenyl) | + | Bupranolol |
| (4-hydroxy-benzofuran-chromone with CH3) | + | Butocrolol |
| CH3(CH2)2−C(=O)−(2-methyl-4-fluorophenyl) | + | Butofilolol |
| (carbazole with CH3) | —⟨ | Carazolol |
| (5-methyl-3,4-dihydroquinolin-2(1H)-one) | + | Carteolol |
| (carbazole with CH3) | CH2CH2O— (2-methoxyphenyl)-CH3O | Carvedilol |
| (4-methyl-3-acetyl-phenyl with Et2NCOHN−) | + | Celiprolol |
| (2-methylphenyl with OCH2CONHCH3) | + | Cetamolol |
| cyclopropyl−CH2OCH2CH2O−(4-methylphenyl) | —⟨ | Cidoprolol |
| (2,4-dichlorophenyl with CH3) | + | Cloranolol |

-continued

| Structure | Group | Name |
|---|---|---|
| 3-COCH₃, 4-CH₃, (CH₃COHN at 5)-phenyl | ⟨ (isopropyl) | Diacetolol |
| 2-cyclohexyl-6-methyl-phenyl | ⟨ (isopropyl) | Exaprolol |
| Fluoren-9-ylidene =N—O— | + (tert-butyl) | IPS-339 |
| 4-methyl-indan-7-yl | ⟨ (isopropyl) | Indenolol |
| 3-chloro-2-methyl-4-methyl-1H-indol-7-yl | propoxyphenyl | Indopanolol |
| 3-methyl-5-(2-(2-methylphenyl)vinyl)isoxazole | + (tert-butyl) | Isoxaprolol |
| 5-methyl-1-oxo-1,2,3,4-tetrahydronaphthalen-8-yl | + (tert-butyl) | Levobunolol |
| 2-methyl-4-methyl-1H-indol-7-yl | ⟨ (isopropyl) | Mepindolol |
| 2,4,6-trimethyl-3-(methoxycarbonyl)phenyl | ⟨ (isopropyl) | Metipranolol |

-continued
| | | |
|---|---|---|
| 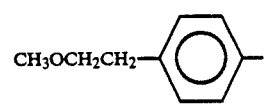 |  | Metoprolol |
| 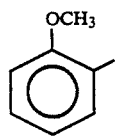 |  | Moprolol |
| 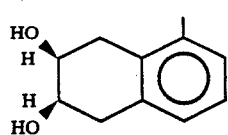 |  | Nadolol |
| 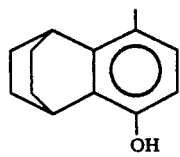 |  | Nafetolol |
| 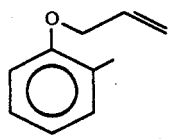 |  | Oxprenolol |
| 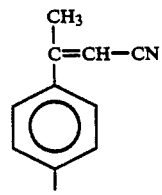 | 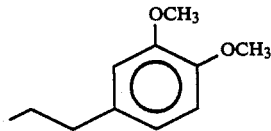 | Pacrinolol |
|  |  | Pafenolol |
| 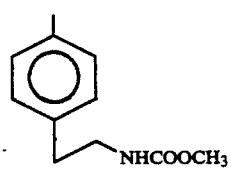 |  | Pamatolol |
| 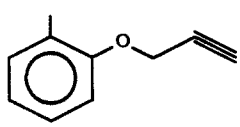 |  | Pargolol |
| 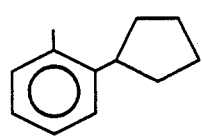 |  | Penbutolol |

-continued
| | | |
|---|---|---|
| 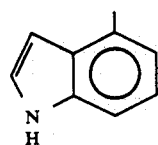 |  | Pindolol |
| 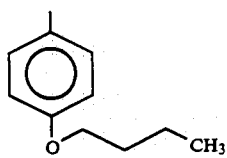 | 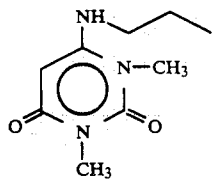 | Pirepolol |
| 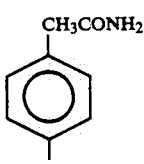 |  | Practolol |
| 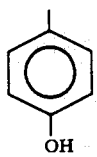 |  | Prenalterol |
| 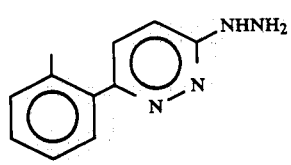 |  | Prizidilol |
| 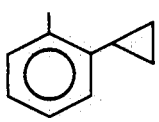 |  | Procinolol |
| 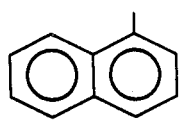 |  | Propranolol |
| 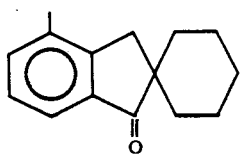 |  | Spirendolol |
| 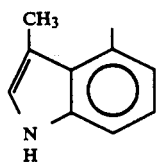 | 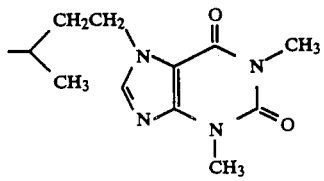 | Teoprolol |
| 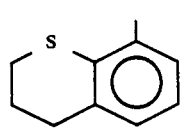 |  | Tertatolol |

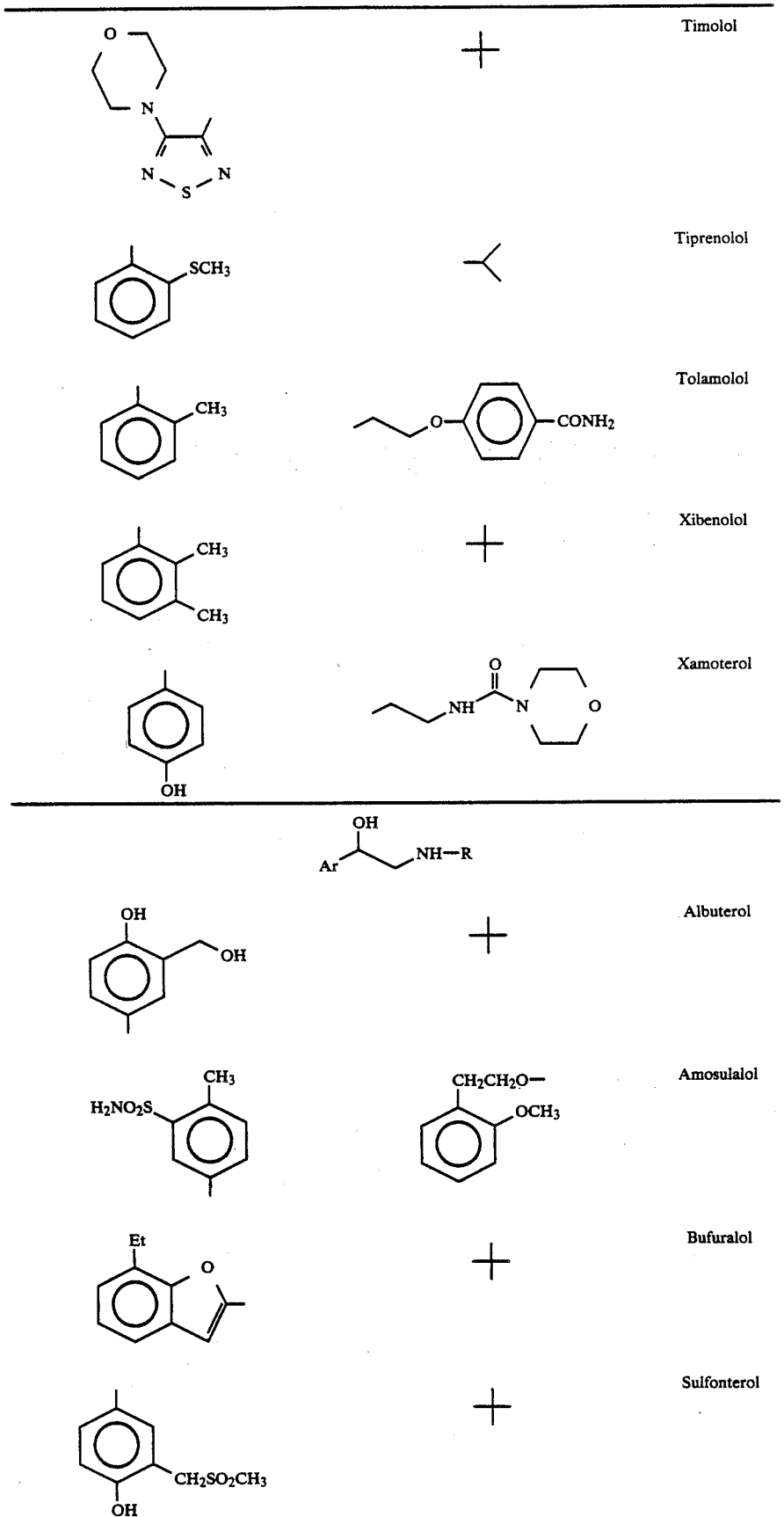

| -continued | |
|---|---|
| 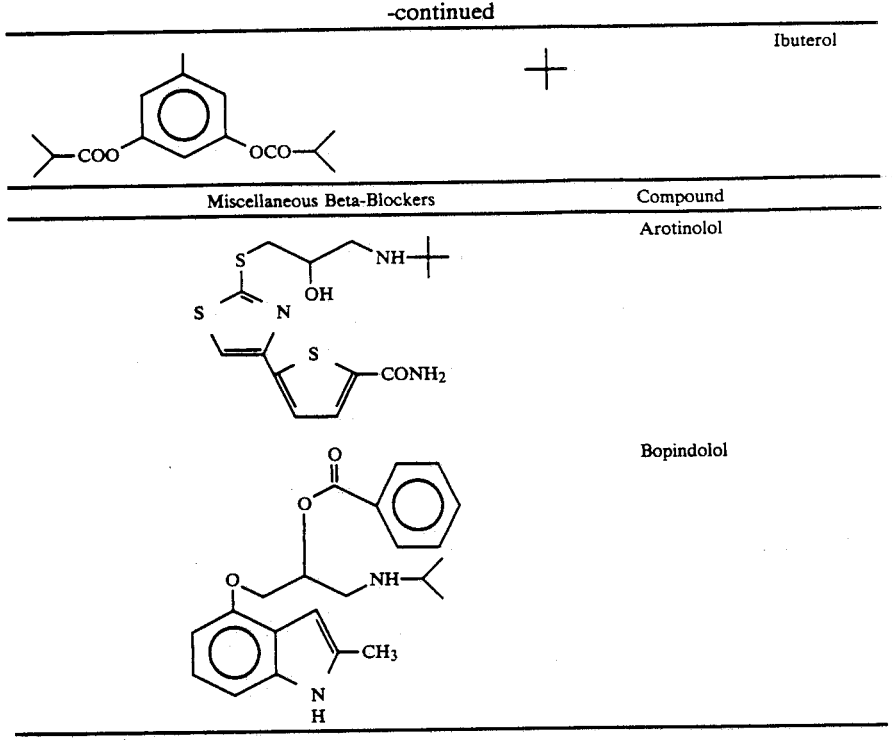 | Ibuterol |
| Miscellaneous Beta-Blockers | Compound |
| | Arotinolol |
| | Bopindolol |

In order to illustrate the manner in which the above compounds may be made, reference is made to the following examples, which, however, are not meant to limit or restrict the scope of the invention in any respect.

EXAMPLE 1

Preparation of (R)-(−)-2-(1-Naphthyloxy-3-bromo)propyl acetate

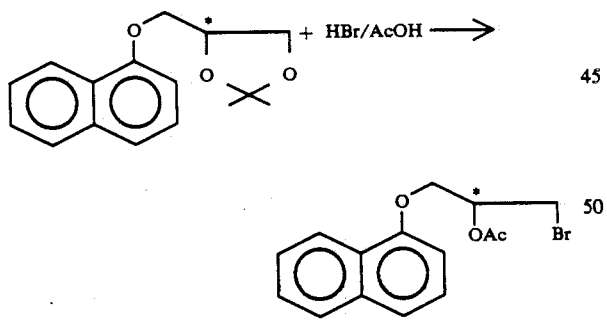

A mixture of (R)-(−)-2,2-dimethyl-4-napthyloxymethyl-1,3-dioxolane (100 g. 0.38 m), 30% HBr/AcOH (150 g) and AcOH (200 g) was allowed to stand at room temperature of 2 hours. Cyclohexane (1 L) was then added. The resulting mixture was stirred and cooled in an ice bath. The K$_2$CO$_3$ (300 g) was added portionwise. After the addition was completed, stirring was continued for 30 minutes. Ice water was then added slowly. The aqueous layer was discarded and the organic layer was further washed with a saturated solution of NaHCO$_3$. The extract was dried over MgSO$_4$ and evaporated to an oil (120 g, 96%). This was used in the next step without any further purification.

EXAMPLE 2

Preparation of (S)-(−)-propranolol-Method A

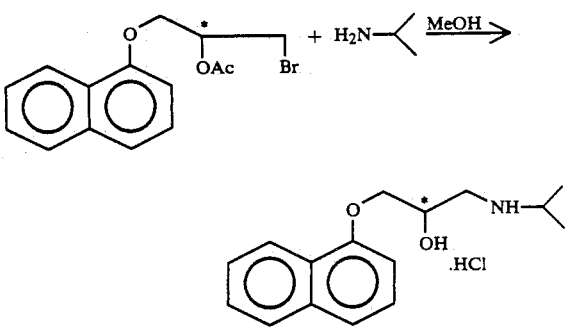

A solution of (R)-(−)-2-(1-napthyloxy-3-bromo)propyl acetate (20 g, 6.2 mM) and ispropylamine (5 g) in methanol (50 mL) was refluxed for 1 hour and evaporated to dryness. The residue was taken up with water, basified with K$_2$CO$_3$ *l and extracted twice with ether. The organic layers were combined, washed with water, dried over MgSO$_4$*, filtered and acidified with hydrogen chloride. The solid precipitate was filtered and recrystallized from ethanol to afford 14.6 g (79.6%) of white crystalline product, m.p. 197°-200° C., $\alpha_D^{25} = -26.1$ (c 1, EtOH).

EXAMPLE 3

Preparation of (S)-(+)-glycidyl napththyl ether

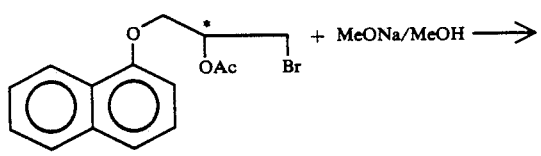

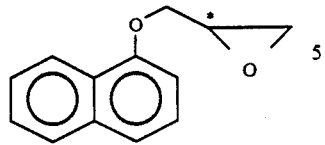

To a solution of (R)-(−)-2(1-napthyloxy-3-bromo)-propyl acetate (120 g, 0.37 m) in methanol (50 mL) was added a solution of 25% MeONa in methanol (96 g). Sodium bromide was separated instantaneously. After stirring for 30 minutes, cyclohexane (1 L) was added to the mixture which was washed twice with water. The organic layer was dried over MgSO$_4$ and evaporated to an oil (70 g, 95%). The crude material was distilled under reduced pressure to yield 62 g (85%) of pure product, bp 130°–135° C. (0.1–0.2 mmHg), $[\alpha]_D^{25}$ +27.1 (c 1.1, EtOH). NMR and IR were consistent with the assigned structure.

EXAMPLE 4

Preparation of (S)-(−)-propranolol-Method B

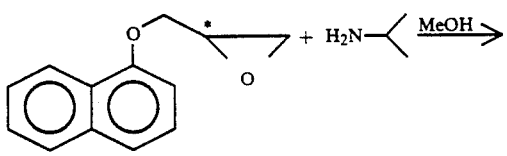

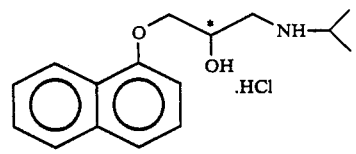

A solution of (S)-(+)-glycidyl naphthyl ether (20 g, 0.1 m) and isopropylamine (10 g, 0.17 m) in methanol (100 mL) was refluxed for 1 hour and evaporated to dryness. The residue was taken up with ether (200 mL), washed with water and dried over MgSO$_4$. After filtering, the filtrate was acidified with gaseous HCl. The crude solid was recrystallized from ethanol to afford 24 g (81%) of pure 1-propranolol, mp 198°–200° C., $[\alpha]_D^{25}$ −26.8 (c 1, EtOH). NMR and IR were consistent with the assigned structure.

Using the same procedures as described in the above examples, the following compounds were prepared:

| Compound | B.p., °C. (M.p.) | $[\alpha]_D^{25}$ |
|---|---|---|
| [structure: R-(−) isoxazole-thiadiazole derivative with CH$_2$CH$_2$O$_2$C group] | 150–160 (0.1–0.2 mmHg) | −7.76 (neat) |
| [structure: R-(−) phenyl derivative with CO$_2$CH$_3$ group] | 152–164 (0.1–0.3 mmHg) | −5.42 (neat) |
| [structure: R-(−) phenyl derivative with CH$_3$CH$_2$O$_2$C group] | 150–165 (1.2–1.8 mmHg) | −18.6 (c 1, EtOH) |

-continued

| Compound | B.p., °C. (M.p.) | $[\alpha]_D^{25}$ |
|---|---|---|
| CH₃CH₂O₂C—[thiadiazole with ethyl ester and glycidyloxy substituents]—S-(+) | 118–122 (0.2 mmHg) | +25.3 (c 1.5, EtOH) |
| [4-(glycidyloxy)phenyl propanoate methyl ester] S-(+) | 150–156 (0.1–0.15 mmHg) | +7.9 (c 0.66, MeOH) |
| CH₃CH₂O₂C—[2-(glycidyloxy)phenyl propanoate ethyl ester] S-(+) | 140–155 (1.0–1.5 mmHg) | +13.08 (c 15, EtOH) |
| CH₃CH₂O₂C—[thiadiazole with 2-acetoxy-3-bromopropoxy substituent] R-(−) | Decomposed | — |
| [4-(2-acetoxy-3-bromopropoxy)phenyl propanoate methyl ester] R-(−) | Decomposed | — |
| CH₃CH₂O₂C—[2-(2-acetoxy-3-bromopropoxy)phenyl propanoate ethyl ester] R-(−) | 165–175 (1.00 mmHg) | −8.3 (c 14, EtOH) |
| CH₃CH₂O₂C—[thiadiazole with 3-tert-butylamino-2-hydroxypropoxy substituent]·N.Maleic Acid S-(−) | (115–118) | −10.5 (c 1, EtOH) |

| Compound | B.p., °C. (M.p.) | $[\alpha]_D^{25}$ |
|---|---|---|
| 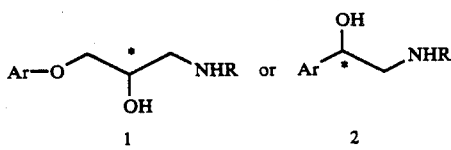<br>S-(−) | (92–94) | −19.6 (c 1, MeOH) |
| 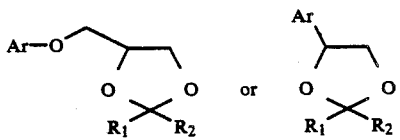<br>S-(−) | (100–102) | −20.3 (c 1, EtOH) |

What is claimed is:

1. A method of preparing a racemic or chiral aryloxypropanolamine (1) of chiral arylethanolamine (2) of the formula

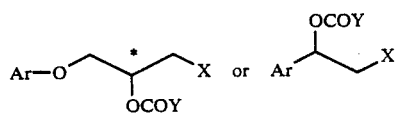

wherein Ar is aryl, substituted aryl, heteroaryl, or aralkyl and R is alkyl, aryl, aralkyl, or EG wherein E is a straight or branched chain alkylene of from 1 to about 6 carbon atoms and wherein G is —$NR_2COR_3$, —$NR_2CONR_3R_4$, —$NR_2SO_2R_3$, —$NR_2SO_2NR_3R_4$, or —$NR_2COOR_5$, where $R_2$, $R_3$, $R_4$, and $R_5$ may be the same or different and may be hydrogen, alkyl, alkoxyalkyl, alkoxyaryl, cycloalkyl, alkenyl, alkynyl, aryl, heteroaryl, or aralkyl, except that $R_3$ and $R_5$ are not hydrogen when G is —$NR_2SO_2R_3$ or —$NR_2COOR_5$, or $R_3$ and $R_4$ may together with N form a 5- to 7-membered heterocyclic group, which method comprises: reacting a selected racemic or chiral dioxolane of the formula

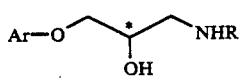

wherein Ar is defined as above and $R_1$ and $R_2$ are each independently hydrogen, loweralkyl, cycloloweralkyl, or $R_1$ and $R_2$ together with the carbon atom form a 3 to 6 member cycloalkyl group or aryl group, with a solution of HX, wherein X is chloro, bromo or iodo, in an organic acid of the formula Y-COOH wherein Y is hydrogen, loweralkyl or cycloalkyl to prepare a racemic or chiral compound of the formula

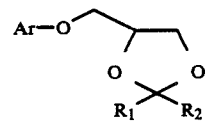

wherein X and Y are as defined above, and reacting said compound with a selected amine to prepare the desired aryloxypropanolamine or arylethanolamine.

2. A method of preparing a racemic or chiral aryloxypropanolamine of the formula $$Ar-O\overset{*}{\underset{OH}{-}}NHR \qquad 1$$

wherein Ar is aryl, substituted aryl, heteroaryl, or aralkyl and R is alkyl, aryl, aralkyl, or EG wherein E is a straight or branched chain alkylene of from 1 to about 6 carbon atoms and wherein G is —$NR_2COR_3$, —$NR_2CONR_3R_4$, —$NR_2SO_2R_3$, —$NR_2SO_2NR_3R_4$, or —$NR_2COOR_5$, where $R_2$, $R_3$, $R_4$, and $R_5$ may be the same or different and may be hydrogen, alkyl, alkoxyalkyl, alkoxyaryl, cycloalkyl, alkenyl, alkynyl, aryl, heteroaryl, or aralkyl, except that $R_3$ and $R_5$ are not hydrogen when G is —$NR_2SO_2R_3$ or —$NR_2COOR_5$, or $R_3$ and $R_4$ may together with N form a 5- to 7-membered heterocyclic group, which method comprises: reacting a selected racemic or chiral dioxolane of the formula $$Ar-O\diagdown\diagup\diagdown\diagup\diagdown$$

wherein Ar is defined in above and $R_1$ and $R_2$ are each independently hydrogen, loweralkyl, cycloloweralkyl, or $R_1$ and $R_2$ together with the carbon atom form a 3 to 6 member cycloalkyl group or aryl group, with a solution of HX, wherein X is chloro, bromo or iodo, in an organic acid of the formula Y-COOH wherein Y is hydrogen, loweralkyl or cyclalkyl to prepare a racemic or chiral compound of the formula

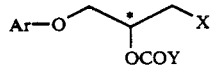

wherein X and Y are as defined above, and reacting said compound with a selected amine to prepare the desired aryloxypropanolamine.

3. A method of preparing a compound of the formula

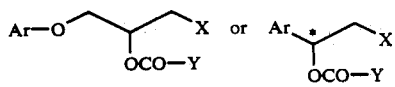

where Ar is aryl, substituted aryl, heteroaryl, or aralkyl, X is chloro, bromo or iodo and Y is hydrogen, loweralkyl or cycloloweralkyl, which method comprises: reacting a selected racemic or chiral dioxolane of the formula

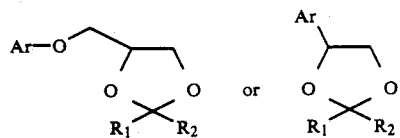

wherein Ar is defined as above and $R_1$ and $R_2$ are each independently hydrogen, loweralkyl, cycloweralkyl, or $R_1$ and $R_2$ together with the carbon atom form a 3 to 6 member cyclalkyl group or aryl group, with a solution of HX, wherein X is defined as above, in an organic acid of the formula Y-COOH wherein Y is defined as above.

4. The method of claim 3 wherein the mixture of strong acid of the formula HX in the organic acid of the formula Y-COOH comprises from 0.1 to 50% strong acid.

5. The method of claim 3 wherein the strong acid is HBr and the organic acid is acetic acid.

6. The method of claim 5 wherein the HBr is present in the acetic acid in an amount of from 0.1 to 50% of the mixture.

7. A method of preparing a racemic or chiral aryloxypropanolamine (1) or chiral arylethanolamine (2) of the formula

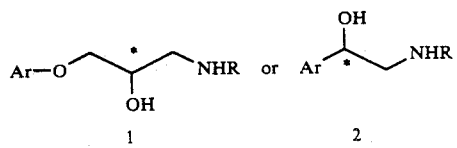

wherein Ar is aryl, substituted aryl, heteroaryl, or aralkyl and R is alkyl, aryl, aralkyl, or EG wherein E is a straight or branched chain alkylene of from 1 to about 6 carbon atoms and wherein G is $-NR_2COR_3$, $-NR_2CONR_3R_4$, $-NR_2SO_2R_3$, $-NR_2SO_2NR_3R_4$, or $-NR_2COOR_5$, where $R_2$, $R_3$, $R_4$, and $R_5$ may be the same or different and may be hydrogen, alkyl, alkoxyalkyl, alkoxyaryl, cycloalkyl, alkenyl, alkynyl, aryl, heteroaryl, or aralkyl, except that $R_3$ and $R_5$ are not hydrogen when G is $-NR_2SO_2R_3$ or $-NR_2COOR_5$, or $R_3$ and $R_4$ may together with N form a 5- to 7-membered heterocyclic group, which method comprises: reacting a selected racemic or chiral dioxolane of the formula

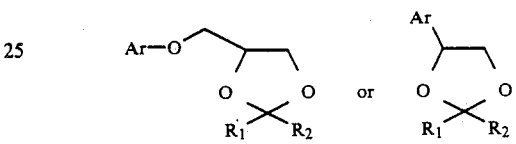

wherein Ar is defined as above and $R_1$ and $R_2$ are each independently hydrogen, loweralkyl, cycloloweralkyl, or $R_1$ and $R_2$ together with the carbon atom form a 3 to 6 member cycloalkyl group or aryl group, with a solution of HX, wherein X is chloro, bromo or iodo, in an organic acid of the formula Y-COOH wherein Y is hydrogen, loweralkyl or cycloalkyl to prepare a racemic or chiral compound of the formula

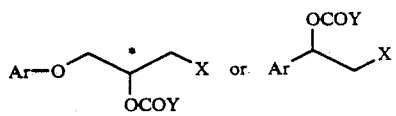

wherein X and Y are defined above, reacting said compound with a suitable base to prepare the appropriate epoxide, and reacting said epoxide with a selected amine to prepare the desired aryloxypropanolamine or arylethanolamine.

* * * * *